United States Patent [19]

Tanaka et al.

[11] Patent Number: 4,816,888
[45] Date of Patent: Mar. 28, 1989

[54] SENSOR

[75] Inventors: Junichi Tanaka; Masaya Hijikigawa, both of Nara, Japan

[73] Assignee: Sharp Kabushiki Kaisha, Osaka, Japan

[21] Appl. No.: 948,409

[22] Filed: Dec. 30, 1986

Related U.S. Application Data

[63] Continuation of Ser. No. 735,689, May 20, 1985, abandoned.

[30] Foreign Application Priority Data

May 31, 1984 [JP] Japan ................................. 59-112736

[51] Int. Cl.$^4$ ............................................. H01L 29/66
[52] U.S. Cl. ..................................... 357/25; 357/23.1; 357/23.6; 357/55; 357/71
[58] Field of Search ....................... 357/234, 25, 71, 55

[56] References Cited

U.S. PATENT DOCUMENTS

| | | | |
|---|---|---|---|
| 3,978,517 | 8/1976 | Brown | 357/71 |
| 4,319,258 | 3/1982 | Harnagel et al. | 357/71 |
| 4,508,613 | 4/1985 | Busta et al. | 357/25 |
| 4,514,751 | 4/1985 | Bhattacharya | 357/71 |
| 4,520,413 | 5/1985 | Piotrowski et al. | 357/23.15 |
| 4,612,560 | 9/1986 | Dortu et al. | 357/23.14 |

FOREIGN PATENT DOCUMENTS

| | | | |
|---|---|---|---|
| 0039174 | 11/1981 | European Pat. Off. | 357/71 |
| 2407110 | 8/1976 | Fed. Rep. of Germany | 357/71 |
| 3032476 | 4/1982 | Fed. Rep. of Germany | 357/71 |
| 1082317 | 9/1967 | United Kingdom | 357/71 |
| 1176582 | 1/1970 | United Kingdom | 357/71 |
| 1586011 | 3/1981 | United Kingdom | 357/71 |

Primary Examiner—Edward J. Wojciechowicz
Attorney, Agent, or Firm—Spencer & Frank

[57] ABSTRACT

A sensor having an electrode structure which comprises a lamination of at least two layers composed of a titanium layer bound to an insulating grounding layer and a nobel metal layer covering said titanium layer.

4 Claims, 1 Drawing Sheet

SENSOR

This application is a continuation of application Ser. No. 735,689, filed May 20, 1985, now abandoned.

BACKGROUND OF THE INVENTION

1. Field of the Invention

This invention relates to a sensor, especially an electrode structure in a field effect transistor type sensor.

2. Description of the Prior Art

A field effect transistor (hereinafter, referred to as FET) type sensor, which comprises an FET device incorporated with a sensitive means exhibiting an electric variation of electrostatic capacity, electric conductivity, electrostatic potential, etc., due to a physical or chemical interaction with the physical quantity to be detected, detects the said physical quantity as a variation of the gate operation of the said FET device. Taking advantage of the high input impedance and the amplifying function of the FET device, such an FET type sensor can exhibit a high output, even though its size is extremely small, and thus is advantageous in actual use. For the incorporation of an FET device with a sensitive means, electrodes are required to be formed on a substrate containing silicon oxide or silicon nitride. Thus, for materials for the electrodes must tightly bind to silicon oxide and/or silicon nitride.

On the other hand, depending upon the kind of sensitive means required, the sensitive means is formed on the electrodes in an atmosphere at a high temperature and/or a high humidity. Thus, the electrode materials must be stable to such an atmosphere. Moreover, since the FET type sensor, which is designed to be used as a gas sensor, a moisture sensor, an ion sensor, a biological sensor, etc., is exposed to an atmosphere due to the necessity of an interaction between the atmosphere and the sensitive means, the electrode materials must be also stable to the atmosphere.

Although aluminium, etc., which is used as an under-gate electrode in the FET device, is excellent in binding to the gate insulating film such as silicon oxide, silicon nitride, etc. it is readily oxidized or corroded in a high temperature and/or high humidity atmosphere or in an external atmosphere. This, aluminium, etc., is not suitable for an electrode material to be used for sensors. On the other hand, noble metals, such as platinum, gold, silver, etc., are stable in a high temperature and high humidity atmosphere and in an external atmosphere, but are inferior in binding to silicon oxide, silicon nitride, etc., and thus are not suitable for electrode materials for FTt type sensors.

SUMMARY OF THE INVENTION

The sensor of this invention which overcomes the above-discussed disadvantages and other numerous drawbacks and defficiencies of the prior art, has an electrode structure which comprises a lamination of at least two layers composed of a titanium layer bound to an insulating grounding layer and a noble metal layer covering said titanium layer.

The electrode structure constitutes electrodes in a field effect transistor which is incorporated with a sensitive means. The noble metal layer is made of gold.

Thus, the invention described herein makes possible the objects of (1) providing a novel sensor having an electrode structure which is not corroded or damaged in a severe environment such as high temperature and high humidity; (2) providing a novel sensor having an electrode structure which is excellent in bonding to a grounding layer to ensure stable operation; (3) providing a novel sensor having an electrode structure which can be stably incorporated into the sensor structure; for instance, when the electrode structure is incorporated into the FET device, it is tightly bound to the gate insulating film such as silicon oxide, silicon nitride, etc., and is stable in an external atmosphere in which the sensitive means is formed and to which the resulting FET type sensor is exposed in the use thereof.

BRIEF DESCRIPTION OF THE DRAWINGS

This invention may be better understood and its numerous objects and advantages will become apparent to those skilled in the art by reference to the accompanying drawings as follows.

DESCRIPTION OF THE PREFERRED EMBODIMENTS

Figure 1:
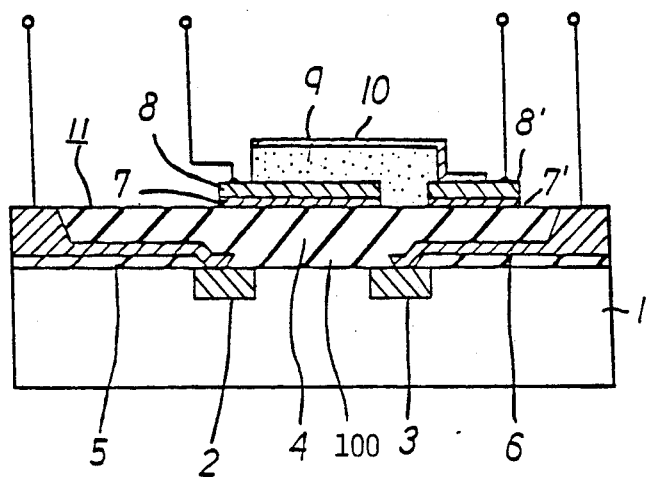
FIG. 1 is a sectional front view showing an FET type moisture sensor according to this invention.

FIG. 1 shows an FET type moisture sensor as an embodiment of the FET type sensor according to this invention, which comprises an FET device 11 incorporated with a sensitive means 9.

The FET device 11 is a MOS-type n-channel FET in which an n-type source 2 and an n-type drain 3 are formed in a row by the diffusion of phosphorus into the surface of a p-type silicon substrate 1. The surface of the silicon substrate 1, is covered with a silicon dioxide insulating film 4 containing through-holes for the source 2 and the drain 3. The portion of the insulating film 4 which is formed on the silicon substrate 1 between the source 2 and the drain 3 forms a gate insulating film 100. A source electrode 5 and a drain electrode 6, each of which comes into contact with the source 2 and the drain 3 at one of their ends, are buried in the insulating film 4. The other ends of each of the source and the drain electrodes 5 and 6 are connected to an external circuit at the ends of the silicon substrate 1, respectively.

On the gate insulating film 100 of the insulating film 4, a titanium layer 7 having a thickness of 500 Å and a gold layer 8 having a thickness of 5000 Å are successively formed by a vacuum evaporation method. The titanium layer 7 and the gold layer 8 are patterned by a lift-off method to form an under-gate electrode. Lamination consisting of two layers of a titanium layer 7' and a gold layer 8' is diposed in a row on a portion of the insulating layer 4 other than the gate insulating film 100 in the same manner as the above-mentioned under-gate electrode, resulting in a bonding pad. The under-gate electrode 7, 8 and the bonding pad 7', 8' can be simultaneously formed by a lift-off method. A moisture sensitive means 9 is disposed in a manner to cover the under-gate electrode 7, 8 and to come into contact with an end of the bonding pad 7', 8'. The moisture sensitive means 9 is covered with a moisture permeable upper-front electrode 10, an end of which is extended at the side of the moisture sensitive means 9 to be connected to the bonding pad. The bonding pad is connected to a control circuit.

The moisture sensitive means 9 is made of polyvinylalcohol or cellulose acetate crystallized by a baking treatment, but is not limited thereto. An organic or inorganic solid electrolyte film, a metal oxide film such as an aluminium oxide film, etc., can be used therefor.

The moisture permeable upper-front electrode 10 is made of a gold evaporation film having a thickness of about 100 Å, but is not limited thereto. The moisture sensitive means 9 is not limited to a moisture sensitive means, but may be a gas sensitive means, an ion sensitive means, another chemical substance sensitive means, a heat sensitive means, a light sensitive means, etc. As the FET device, a MIS-type FET can be used.

When an electric current flows from the source electrode 5 to the drain electrode 6, the current obtained in the drain electrode 6 varies depending upon a variation of the voltage in the under-gate electrode based on the characteristic of the FET device 11. The under-gate electrode is connected to the upper-front electrode 10 by the moisture sensitive means 9 and a given potential is applied to the upper-front electrode 10 through the bonding pad by the external control circuit. The impedance of the moisture sensitive means 9 varies with the humidity in the surrounding atmosphere, and thus the voltage in the undergate electrode 7, 8 varies with the impedance variation in the moisture sensitive means 9, resulting in a variation of the current in the drain electrode. By detecting the current, the humidity in the surrounding atmosphere can be determined.

Electric charges tend to be accumulated in the same direction in the moisture sensitive means 9 depending upon the operation period, causing non-uniform gate voltage which results in a decrease in measurement accuracy. In order to eliminate the problem, according to this embodiment, a refreshing potential is directly applied to the under-gate electrode by an external circuit to remove such accumulated electric charges from the moisture sensitive means 9.

As mentioned above, the under-gate electrode and the bonding pad are composed of a double layered structure of the titanium layers 7 and 7' and the gold layers 8 and 8'. The adhesion between each of the titanium layers 7 and 7' and the insulating layer 4 is excellent and moreover, the titanium layers 7 and 7' are coated with the gold layers 8 and 8', respectively, so that the electrode structure is stable in a high temperature and/or a high humidity atmosphere and in an external atmosphere. Instead of the gold layers 8 and 8', noble metal layers such as platinum, silver, etc., can be employed.

The electrode structure was subjected to a pressure cooker test at 120° C. for 96 hours under 2 atmospheres to accelerate deterioration thereof, but neither the separation of electrodes from the insulating film nor the variation of resistance values could be observed.

The above-mentioned electrode structure is not limited to the application to FET type sensors, but can be widely applied to grounding layer materials such as silicon oxide, silicon nitride, glass, ceramics, etc.

It is understood that various other modifications will be apparent to and can be readily made by those skilled in the art without departing from the scope and spirit of this invention. Accordingly, it is not intended that the scope of the claims appended hereto be limited to the description as set forth herein, but rather that the claims be construed as encompassing all the features of patentable novelty which reside in the present invention, including all features which would be treated as equivalents thereof by those skilled in the art to which this invention pertains.

What is claimed is:

1. A field effect transistor type sensor for detecting a physical condition of the surrounding atmosphere comprising: a field effect transistor including a semiconductor body having spaced source and drain regions disposed in one major surface of the semiconductor body and defining a channel region between said source and drain regions, an insulating layer of silicon oxide or silicon nitride covering said one major surface, a gate electrode disposed directly on the outer surface of said insulating layer overlying said channel region, respective source and drain electrodes for said source and drain regions, and electrical contacts for said source, drain and gate electrodes; a condition sensitive dielectric layer, whose electrostatic capacity or resistance varies in response to a physical condition which is to be sensed in the atmosphere surrounding the sensor, disposed directly on said gate electrode and overlying said channel region; a further electrode disposed on at least the outer major surface of said condition sensitive dielectric layer; and means for electrically contacting said further electrode including a bonding pad disposed on a portion of said outer surface of said insulating layer which is laterally spaced from said gate electrode so that it does not overlie said channel region, with said bonding pad being comprised of a lamination of at least two layers including a titanium layer bound to said insulating layer and an outer layer of a noble metal covering said titanium layer; and wherein said gate electrode has an electrode structure which comprises a lamination of at least two layers composed of a titanium layer bound to said insulating layer and an outer noble metal layer covering said titanium layer, at least said condition sensitive dielectric layer and said further electrode are exposed to the surrounding atmosphere, said condition responsive layer extends to said outer surface of said insulating layer between said gate electrode and said bonding pad and extends laterally along said outer surface of said insulating layer to said bonding pad, and said further electrode extends over said condition responsive layer to said bonding pad and ohmically contacts same.

2. A sensor as defined in claim 1, wherein said noble metal layer is made of gold.

3. A sensor as defined in claim 1, wherein said noble metal layer is made of silver or platinum.

4. A sensor as defined in claim 1 wherein: said source and drain electrodes extend via respective openings in said insulating layer from the respective said source and drain regions to said outer surface of said insulating layer and have respective portions disposed within said openings which are oriented substantially parallel to said one major surface of said semiconductor body; and said portion of said outer surface of said insulating layer on which said bonding pad is disposed overlies said portion of said drain electrode which extends substantially parallel to said one major surface of said semiconductor body.

* * * * *